US006218662B1

(12) United States Patent
Tchakarov et al.

(10) Patent No.: US 6,218,662 B1
(45) Date of Patent: Apr. 17, 2001

(54) DOWNHOLE CARBON DIOXIDE GAS ANALYZER

(75) Inventors: Borislav J. Tchakarov, Katy; Rocco DiFoggio, Houston; Stanislav W. Forgang, Houston; Otto N. Fanini, Houston; James C. Hunziker, New Caney; Marcelo F. Civarolo, Katy, all of TX (US)

(73) Assignee: Western Atlas International, Inc., Houston, TX (US)

( * ) Notice: Subject to any disclaimer, the term of this patent is extended or adjusted under 35 U.S.C. 154(b) by 0 days.

(21) Appl. No.: 09/065,159

(22) Filed: Apr. 23, 1998

(51) Int. Cl.[7] .................................................. G01N 21/59
(52) U.S. Cl. ...................... 250/256; 250/255; 250/338.1; 250/340; 250/343
(58) Field of Search .................................... 250/256, 255, 250/258, 261, 343, 338.1, 339.01, 339.06, 339.12, 339.13, 340

(56) References Cited

U.S. PATENT DOCUMENTS

| 4,160,373 | * | 7/1979 | Fastaia et al. | 73/23 |
|---|---|---|---|---|
| 4,297,088 | * | 10/1981 | Akkerman | 417/378 |
| 5,068,770 | * | 11/1991 | Baziuk | 362/61 |
| 5,332,901 | * | 7/1994 | Eckles et al. | 250/345 |
| 5,340,987 | * | 8/1994 | Eckles et al. | 250/345 |
| 5,357,113 | * | 10/1994 | Liston et al. | 250/344 |
| 5,457,320 | * | 10/1995 | Eckles et al. | 250/345 |
| 5,464,982 | * | 11/1995 | Drucker et al. | 250/343 |
| 5,559,333 | * | 9/1996 | Araya et al. | 250/344 |

* cited by examiner

*Primary Examiner*—Constantine Hannaher
(74) *Attorney, Agent, or Firm*—Darryl M. Springs

(57) ABSTRACT

A logging tool system for analyzing the carbon dioxide concentration in a fluid sample downhole in a borehole. A chamber is filled with the fluid sample and is closed to isolate the fluid sample from the borehole. The interior chamber volume is expanded to decompress the fluid sample, and a transmitter discharges light in the mid-infrared range. A sensor measures the absorbance of mid-infrared light by the decompressed fluid sample and generates a signal representing the carbon dioxide concentration. Mid-infrared light absorbance in the range between 4.1 and 4.4 microns can be analyzed by the processor to identify the carbon dioxide concentration in the fluid sample, and infrared absorbance in the mid-infrared range between 3.2 and 3.6 microns can be analyzed to identify methyl and metheylene components. A wiper cleans the transmitter and sensor between readings to reduce measurement errors caused by fluid sample contamination.

23 Claims, 2 Drawing Sheets

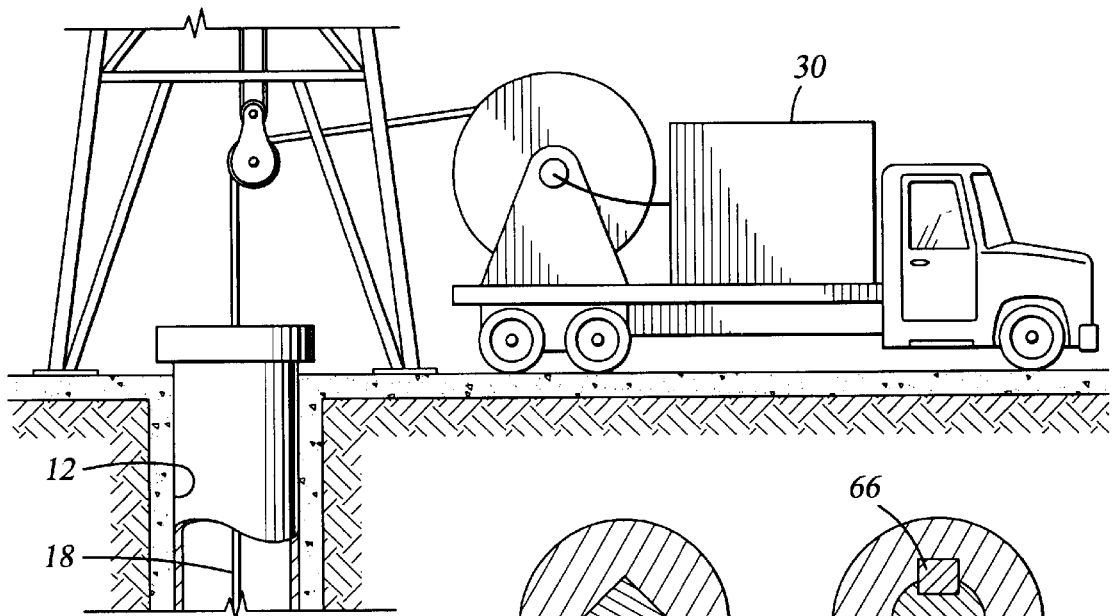
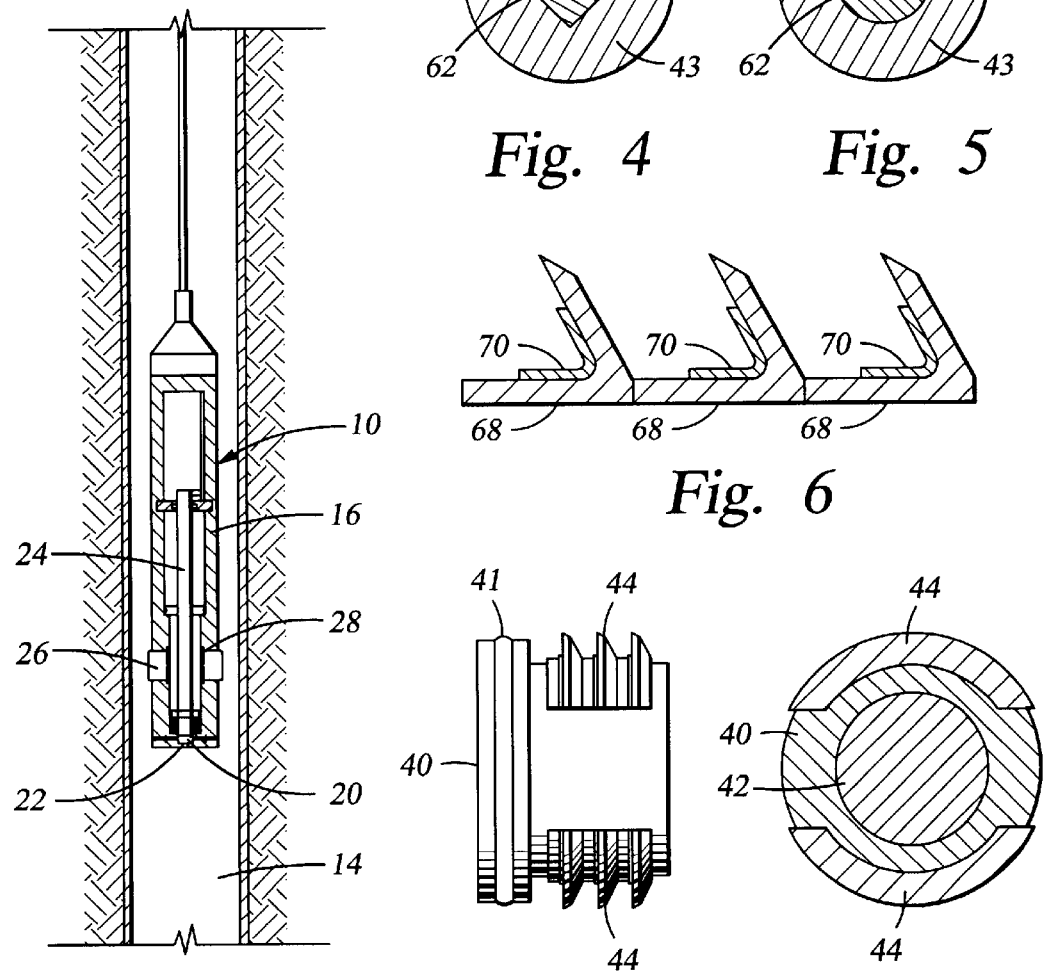
Fig. 1  Fig. 4  Fig. 5  Fig. 6  Fig. 7  Fig. 8

DOWNHOLE CARBON DIOXIDE GAS ANALYZER

BACKGROUND OF THE INVENTION

The present invention relates to the field of gas analysis downhole in a hydrocarbon producing well. More particularly, the present invention relates to a system for analyzing carbon dioxide concentration downhole in a borehole Hydrocarbon producing wells contain numerous formation liquids and gases including methane, ethane, carbon dioxide, hydrogen sulfide, and other gaseous compounds. Deep wells produce fluids at extremely high temperatures. The detection and analysis of gas concentrations provides information useful in evaluating the commercial value of a hydrocarbon producing well. Numerous systems have been developed to evaluate borehole fluid composition and the relative gas concentrations in the borehole fluid.

In U.S. Pat. Nos. 5,167,149 to Mullins et al. (1992) and in U.S. Pat. No. 5,201,220 to Mullins et al. (1993), a borehole apparatus detected the presence of gas within a formation fluid sample. A light source transmitted light to an interface between the fluid sample and a flow line, and a detector array sensed reflected light rays having angles of incidences between the Brewster angle and the critical gas angle. A processor determined the percentage of gas by comparing the detected information to information stored in a data base. The processor also categorized the fluid sample as high gas, medium gas, and low gas.

A method for determining the quantity of dissolved gas in a sample was disclosed n U.S. Pat. No. 5,635,631 to Yesudas et al. (1997), wherein the pressure and volume of a sample were first measured. The sample pressure was changed by expanding he sample until the pressure/volume relationship was non-linear, and the sample was expanded to determine the point at which pressure was unchanged. A bubble point for the sample was determined, and the sample pressure and the bubble point volume was determined. The dissolved gas volume was then calculated by linearly scaling the bubble point volume and the extrapolated sample volume relative to the difference between the second volume and the bubble point volume.

Other systems have been disclosed to evaluate gas composition within a formation fluid. U.S. Pat. No. 4,994,671 to Safinya et al. (1991) disclosed a borehole logging tool for analyzing the composition of formation fluids. Specifically, the apparatus used near infrared spectral analysis to determine quantities of gas, water and oils in a hydrocarbon fluid. A light source emitted near infrared rays in a wavelength range between 0.3 and 2.5 microns, and a spectral detector sensed the spectrum of backscattered and transmitted rays. A data base stored the sensed data, and a processor determined the fluid composition by evaluating the near infrared absorption spectral information. The source spectrum and either the transmitted or backscattered light spectra were compared to known spectral data. After the bubble point or dew point was identified, the low line pressure was increased above such point by controlling the fluid flow rate or by moving the logging tool to an appropriate depth within the borehole.

In certain boreholes containing formation fluids combining various liquids and gases, carbon dioxide occupies substantial volumes relative to the amount of recoverable hydrocarbons. As the formation fluids are produced to the wellbore surface, hydrocarbon gases are separated from the noncommercial carbon dioxide because the economic value of carbon dioxide relative to the hydrocarbons is low. Although carbon dioxide has been historically discharged into the ambient surroundings, global warming issues may discourage this form of gas separation and disposal. Carbon dioxide is also reinjected into subsurface geologic formations, however re-injection wells are expensive and may be impractical in certain geographic regions.

Accordingly, a need exists for a system capable of accurately evaluating the presence and quantity of carbon dioxide downhole in a borehole so that zones containing high levels of carbon dioxide can be avoided. The system should accurately identify the carbon dioxide concentration under different pressures, temperatures and wellbore conditions, and should provide real-time logging capabilities before borehole completions operations are performed.

SUMMARY OF THE INVENTION

The present invention provides an apparatus and method for analyzing the carbon dioxide concentration in a fluid sample downhole in a borehole. The apparatus comprises a chamber defining an initial volume for containing the fluid sample, a means for expanding said chamber initial volume to decompress the fluid sample, and a transmitter for discharging mid-infrared light. A sensor measures the absorption of mid-infrared light by the decompressed fluid sample and generates a signal representing the carbon dioxide concentration in the fluid sample. A processor receives the signal and determines the fluid sample carbon dioxide concentration.

In different embodiments of the apparatus, the sensor can measure infrared absorbance in ranges between 4.1 and 4.4 microns to identify carbon dioxide concentration, and between 3.2 and 3.6 microns to provide data representing methyl and methylene concentrations. The chamber expanding means can expand the chamber initial volume until the fluid sample is substantially one hundred percent gas phase, and a means for cleaning the transmitter and the sensor between successive measurements can reduce measurement errors.

The method of the invention comprising the steps of deploying a chamber into the borehole to define an initial chamber volume, of moving the fluid sample into said chamber volume, of closing said chamber to isolate the fluid sample from the borehole, and of expanding said initial chamber volume to decompress the fluid sample. A transmitter is operated to discharge mid-infrared light, and a sensor is operated to measure the fluid sample mid-infrared light absorbance and to generate a signal representing the carbon dioxide concentration. A processer can receive and store the signal from the sensor. The processor can also be operated to determine the carbon dioxide concentration.

BRIEF DESCRIPTION OF THE DRAWINGS

FIG. 1 illustrates a carbon dioxide logging tool downhole in a wellbore.

FIGS. 4 and 5 illustrate different profiles for the piston shaft.

FIG. 6 illustrates one profile for a wiper seal combination.

FIGS. 7 and 8 illustrate one configuration of a wiper element.

DESCRIPTION OF THE PREFERRED EMBODIMENTS

Figure 2:
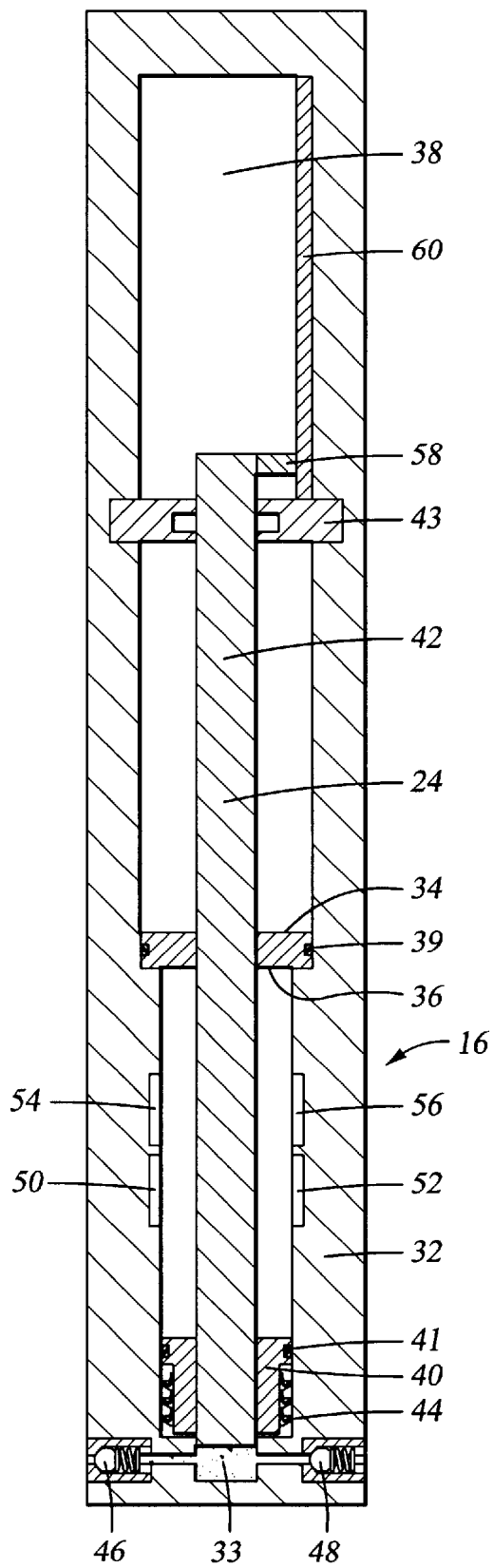
FIG. 2 illustrates a logging tool after a fluid sample is introduced into the interior chamber of the tool.

The present invention provides an apparatus and method for analyzing the carbon dioxide concentration of a fluid sample downhole in a borehole. The invention permits the carbon dioxide concentration to be surveyed downhole so that perforating and well production operations can avoid high carbon dioxide zones, thereby reducing expenses for gas separation, re-injection wells and other production operations.

FIG. 1 illustrates logging tool 10 located downhole in borehole 12. Fluid 14 from subterranean formations flows into borehole 12 and can be selectively produced to the wellbore surface. As used herein, the term "fluid" refers to liquids and gases typically under compression within the subterranean geologic formations. The fluid pressures in deep boreholes can be 20,000 psi or greater, thereby reducing carbon dioxide and other gases to a liquid phase.

Tool 10 comprises housing 16 attached to wireline 18. Housing 16 includes chamber 20 defining an interior space or initial volume 22 having known dimensions. Decompression cylinder shown as hydraulic cylinder 24 defines the size of chamber 20 within housing 16 and is moveable to selectively increase the size of initial volume 22, thereby decompressing any fluid sample initially positioned within initial volume 22 as described below. Transmitter 26 discharges mid-infrared light, and sensor 28 detects midinfrared light that is not backscattered or absorbed by fluid 14. Sensor 28 generates a signal as described below and transmits such signal to processor 30 for receiving, storing and processing the signal or combination of signals.

Figure 3:
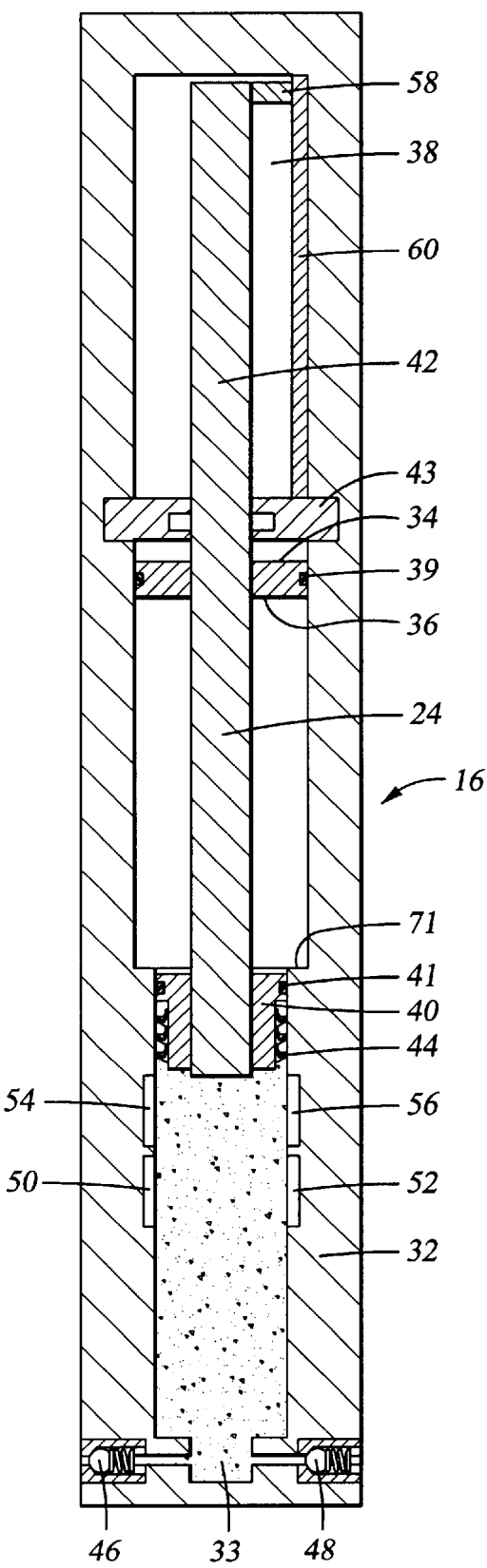
FIG. 3 illustrates the fluid sample within the measurement chamber after the fluid has been decompressed.

Referring to FIG. 2, one embodiment of logging tool 10 is shown. Housing 16 is shown as cylindrical tube 32. Initial volume 33 comprises a relatively small space located at one end of tube 32. Moveable cylinder 34 has piston head 36 movable by a suitable means such as moveable device 38. Piston head 36 includes seal 39 for preventing leakage of hydraulic or another fluid. Device 38 can comprise any hydraulic, mechanical, electrical or similarly powered means for moving piston head 36. Seal 39 attached to piston head 34 and prevents leakage of hydraulic fluid or another fluid through the clearance between piston head 36 and cylindrical tube 32, stop 71, a shown in FIG. 3, is positioned within cylindrical tube 32, and decompression piston 40 having dynamic seal 41 is attached to one end of piston shaft 42. Piston shaft 42 is reciprocal within cylinder tube 32 and is guided by an aperture through stop 39 and by the outer radius of piston head 36. Piston shaft 42 can extend through piston head 36 and is attached to piston head 36 and to wiper 44 so that movement of piston shaft 42 also moves piston head 36 and wiper 44. In one embodiment of the invention as illustrated, wiper 44 is attached to decompression piston 40 or can be integrated into decompression piston 40 in other configurations.

Wiper 44 scrubs the interior wall of cylindrical tube 32 and can cooperate with decompression piston 40 to define the space identified as measurement volume 45. Measurement volume 45 is illustrated in FIG. 3 as the space opened by movement of wiper 44 within cylindrical tube 32, combined with the space defined by initial volume 33. As defined herein, measurement volume 45 provides the final volume for the fluid sample after decompression of the fluid sample is performed.

Inlet valve 46 selectively permits the entry of borehole fluid 14 into initial volume 33, and discharge valve 48 selectively permits the discharge of borehole fluid 14 out of initial volume 33. Although inlet valve 46 and discharge valve 48 could comprise the same valve or valve combination, using two valves permits a flowthrough passage of the fluid sample through initial volume 33 to reduce potential contamination of each fluid sample as successive samples are tested and to avoid commingling of successive samples.

After a fluid sample has been introduced into measurement volume 45 and the sample has been decompressed so that the target gas comprises one hundred percent gaseous phase, the composition of the gas can be assessed. Transmitter 50 is engaged with tube 32 and corresponding sensor 52 is positioned opposite of tube 32. Other combinations of instruments such as transmitter 54 and corresponding sensor 56 can be similarly engaged with tube 32 as described below. Position sensor 58 is attached to piston shaft 42, and reading sensor 60 identifies the relative location of position sensor 58. Different mechanisms for measuring the relative position of shaft 42 can be created to monitor and verify the operation of logging tool 10.

In operation, inlet valve 46 and discharge valve 48 are opened to draw a fluid sample of borehole fluid 14 through interior volume 33. Discharge valve 48 is closed, and inlet valve 46 is then closed to isolate the known fluid sample quantity of fluid 14 at an initial volume correlating to initial volume 33 and to contain the fluid 14 sample. Subsequently, piston shaft 42 and decompression piston 40 are moved to the position shown in FIG. 3. This movement enlarges the space of initial volume 33 into measurement volume 45. This piston shaft 42 movement decompresses the fluid sample by increasing the volume occupied by such fluid sample. The extent of such movement is monitored with position sensor 58 and reading sensor 60 to provide accurate information regarding the decompression of the fluid sample.

The fluid sample decompression allows fluid 14 to change phase partially or completely as desired. If the fluid sample is initially liquid phase at high pressure within borehole 12, decompressing the fluid sample by increasing the fluid sample volume can release the fluid sample into a partial or complete gaseous state. In a preferred embodiment of the invention, the fluid sample is preferably decompressed to a level where the fluid sample is at a pressure below the critical pressure of carbon dioxide so that carbon dioxide within fluid 14 converts one hundred percent from a liquid phase to a gaseous phase.

The relative decompression of the fluid sample can be controlled in different ways. As representative examples, the fluid sample can be decompressed with mechanical, hydraulic or electrical means. In other embodiments of the invention, decompression of a pressurized fluid sample can be accomplished by selectively releasing a measured quantity of fluid 14 into a measurement chamber which has been evacuated with a pump or cylinder mechanism. The decompression amount of the fluid sample can be determined by the ratio of measurement volume 45 versus initial volume 33 occupied by the fluid sample at a known pressure. If decompression is accomplished by introducing a selected quantity of fluid into a vacuum, the decompression of the fluid sample can be controlled by the chamber sizes and the initial fluid quantity.

The initial volume 33 within chamber 20 is illustrated as having a quantifiable space. In different embodiments of the invention, the initial volume can be created in different ways. If cylinder 24 initially closes the entire interior of chamber 20, the initial volume 33 could comprise a minutely small clearance between the end of cylinder 24 and the intake portion of chamber 20, together with the inlet lines between the valves 46 and 48 and cylinder 24. The accuracy of subsequent measurements will depend on the initial fluid sample size, the amount of decompression obtained, the nature of contaminants in the fluid sample, the temperature of the fluid sample, and other variable factors.

After the fluid sample is decompressed to a selected level, transmitters 50 and 54 can discharge light rays in selected wavelength ranges, and sensors 52 and 56 can detect transmitted light rays corresponding to the respective transmitters. In a preferred embodiment of the invention, transmitter 50 discharges mid-infrared light in a range between 4.1 to 4.4 microns. This range comprises a preferred range for carbon dioxide absorbance. Using Beer's Law and assuming a fixed pathlength, the amount of carbon dioxide in the fluid sample is proportional to the absorption of light in this preferred range. In another embodiment of the invention, transmitter 54 discharges mid-infrared light in a range between 3.2 to 3.6 microns, which comprises a preferred range for absorbance of methyl and methylene functional groups. Data collected from these two frequency ranges provides information for precisely determining the ratio of carbon dioxide to hydrocarbon gases predominately comprising methyl and methylene.

The absorbance of emitted light within these ranges is influenced by fluid 14 composition and by environmental factors. At high temperatures, mid-infrared light sensors become noisy. Interference from absorbance by other molecules in the range between 4.1 and 4.4 microns should not interfere with the carbon dioxide measurements because other molecules absorbing light in such range, such as alkynes and nitrites, typically comprise unstable triple-bonded compounds not typically found in natural gas and other downhole formation fluids. If an interfering molecule is resident within the fluid sample, additional wavelengths can be measured with other transmitters and sensors to compensate for and to distinguish the interfering molecule.

By measuring the amount of light detected by sensor 52, the amount of carbon dioxide absorbance within fluid 14 can be determined, and a signal representing this information can be transmitted to processor 30 for storage or for data processing operations. Processor 30 can be operated to determine the carbon dioxide concentration with fluid 14 through the application of processing techniques known in the art. Similarly, a signal generated by sensor 56 can be transmitted to processor 30 for storage and data processing. After the selected measurements are taken, inlet valve 46 and discharge valve 48 are opened, shaft 42 is reciprocated toward the initial position, and the fluid sample is discharged from the interior of logging tool 10. The orientation and operation of discharge valve 48 or a discharge port (not shown) can be positioned to permit throughflow of the fluid sample through logging tool 10 to prevent contamination of fluid 14 measurements.

Referring to FIGS. 4 and 5, various techniques are illustrated for maintaining a constant orientation of shaft 42 relative to the other components, and for maintaining the orientation of wiper 44 relative to transmitters 50 and 54 and sensors 52 and 56. FIG. 4 illustrates a rectangular shaft 62 to accomplish this function, and FIG. 5 illustrates cylindrical shaft 64 linearly guided with key 66 operating within a corresponding slot or keyway (not shown) within stop 43. Other mechanical devices and orientations can be utilized to constrain the movement of shaft 42, or to avoid restraints on the rotational movement of shaft 42.

In various embodiments of the invention, transmitters 50 and 54, and sensors 52 and 56, can be in optical contact with the interior space of cylindrical tube 32 through glass windows or other transparent or translucent materials. When fluid 14 is run into and out of such interior space, contaminants within fluid 14 can be deposited on such materials and can interfere with accurate readings of light transmission and detection. To reduce errors caused by such contaminants, wiper 44 removes fluid 14 contaminants from the surfaces of transmitters 50 and 54 or from the surfaces of sensors 52 and 56. Wiper 44 accomplishes this cleaning means function as shaft 42 is reciprocated in both directions to move wiper 44 within cylindrical tube 32, and can clean the internal components immediately before absorption measurements are performed.

FIG. 6 illustrates detail for one form of wiper 44 wherein seals 68 are attached to shaft 42 and are stacked to provide redundant cleaning capabilities. Seals 68 can be formed with different materials including high temperature high performance polymers such as Peek and Viton, and can comprise different structural shapes and configurations. As shown in FIG. 6, springs 70 can provide structural support for the wiping elements of seals 68. Although seals 68 are oriented in one direction, other seal designs can provide for similar cleaning action regardless of the movement direction of seals 68. Although linear movement of seals 68 is illustrated, rotation of shaft 42 could be performed to accomplish different cleaning movements.

FIG. 7 illustrates one embodiment of decompression piston 40 wherein wiper 44 is attached to decompression piston 40. Although seal 41 can prevent fluid migration past piston 40, seal 41 does not adequately clean transmitters 50 and 54 or sensors 52 and 56. FIG. 8 further illustrates another view of wiper 44 taken in section through wiper 44, and showing one potential orientation relative to shaft 42.

The invention provides a unique apparatus and method for analyzing carbon dioxide concentrations downhole in a borehole. Accordingly, logging operations can be operated real-time before wellbore completion operations are performed. By flushing the fluid sample from the measuring chamber after each cycle, the measurement of each sample is more representative of the sample location at the present logging tool location. By cleaning the surfaces and windows of the transmitters and sensors before each measurement, false readings and other measurement errors are minimized. The apparatus permits decompression of the entrained carbon dioxide to up to one hundred percent expansion, thereby increasing the accuracy of the concentration measurements relative to other compounds in the fluid sample. The apparatus also permits multiple measurements to be made directly for carbon dioxide and for hydrocarbon gases within the fluid sample.

Although the invention has been described in terms of certain preferred embodiments, it will become apparent to those of ordinary skill in the art that modifications and improvements can be made to the inventive concepts herein without departing from the scope of the invention. The embodiments shown herein are merely illustrative of the inventive concepts and should not be interpreted as limiting the scope of the invention.

What is claimed is:

1. A bore hole apparatus for analyzing the carbon dioxide concentration in a fluid sample down hole in a bore hole, comprising:

a decompression chamber having a piston for defining an initial volume in the decompression chamber for containing the fluid sample wherein the piston is slidably disposed within the decompression chamber for controllably expanding the decompression chamber initial volume of the decompression chamber and decreasing the pressure within the decompression chamber to decompress the fluid sample;

a transmitter for discharging mid-infrared light;

a first sensor for measuring the absorption of mid-infrared light by the decompressed fluid sample and for generating a signal representing the carbon dioxide concentration in the fluid sample; and a processor for receiving said signal and for determining the fluid sample carbon dioxide concentration.

2. An apparatus as recited in claim 1, wherein said first sensor measures infrared absorbance in a range suitable for detection of carbon dioxide.

3. An apparatus as recited in claim 2, further comprising a second sensor for measuring infrared absorbance in a range suitable for the detection of selected hydrocarbon gases.

4. An apparatus as recited in claim 3, further comprising a third sensor suitable for detection of an interfering molecule resident within the fluid sample.

5. An apparatus as recited in claim 1, wherein the piston is capable of precisely expanding the expansion chamber initial volume of the fluid sample, and precisely controlling the initial volume of the initial fluid sample until the fluid sample expands to transform to its substantially one hundred percent gas phase.

6. An apparatus as recited in claim 1, further comprising a wiper disposed inside of the decompression chamber for cleaning the inside of the decompression chamber.

7. An apparatus as recited in claim 6, wherein the wiper is attached to the piston so that the wiper cleans the inside of the decompression chamber during at least one of: compression or decompression of the decompression chamber so that at least one of the sensor window and transmitter window is cleaned.

8. An apparatus as recited in claim 7, wherein the wiper comprises at least one blade.

9. An apparatus as recited in claim 8, wherein the wiper blade is spring loaded.

10. An apparatus as recited in claim 1, further comprising a wiper disposed in the decompression chamber, wherein the transmitter and sensor are adjacent the expansion chamber so that the wiper cleans at least one of a transmitter window and sensor window during at least one of: compression and decompression of the decompression chamber.

11. An apparatus as recited in claim 1, wherein a piston and an integrated wiper are integrated in the chamber for selectively expanding the initial chamber volume and for returning the apparatus to the initial chamber volume.

12. A method for analyzing the carbon dioxide concentration in a fluid sample down hole in a bore hole, comprising the steps of:

deploying into a bore hole a housing containing a decompression chamber having a piston and integrated wiper for defining an initial volume in the decompression chamber to define the piston being set to define an initial chamber volume;

receiving a measured quantity of the fluid sample into the initial chamber volume;

closing said chamber to isolate the fluid sample from the bore hole;

expanding said initial chamber volume to decompress the fluid sample;

operating a transmitter to discharge mid-infrared light through the decompressed fluid sample; and operating a sensor to measure the decompressed fluid sample mid-infrared light absorbance and to generate a signal representing the carbon dioxide concentration.

13. The method as recited in claim 12, further comprising the step of operating a processor to receive said signal.

14. The method as recited in claim 13, further comprising the step of operating said processor to store said signal.

15. The method as recited in claim 13, further comprising the step of operating said processor to determine the carbon dioxide concentration.

16. The method as recited in claim 12, wherein said initial chamber volume is expanded until the fluid sample is at a pressure below the critical pressure for transforming carbon dioxide from liquid phase to 100 per cent gas phase.

17. The method as recited in claim 12, wherein said transmitter is operated to discharge mid-infrared light in a range suitable for detection of carbon dioxide.

18. The method as recited in claim 12, further comprising the step of operating a second transmitter to discharge mid-infrared light in a range suitable for detection of hydrocarbon gases.

19. The method as recited in claim 12, further comprising the step of operating a second sensor for measuring mid-infrared light absorbance in a range between 3.2 and 3.6 microns.

20. The method as recited in claim 12, further comprising the step of operating the piston and integrated wiper for cleaning the transmitter and the sensor before the sensor is operated to measure the absorbance of mid-infrared light.

21. The method of claim 12, wherein the initial chamber volume is expanded by extending the piston and wiper substantially positioned with the initial chamber volume in a position outside of the initial chamber volume.

22. The method as recited in claim 12, further comprising the step of cleaning the transmitter and the sensor with the integrated wiper attached to the piston.

23. A method for analyzing the carbon dioxide concentration in a fluid sample down hole in a bore hole, comprising the steps of:

deploying a decompression chamber having a piston and integrated wiper for defining an initial volume in the decompression chamber into the bore hole, the piston being set to define an initial chamber volume;

decompressing the decompression chamber so that a vacuum exists in the decompression chamber;

moving the fluid sample into the evacuated chamber volume;

operating a transmitter to discharge mid-infrared light through the decompressed fluid sample; and operating a sensor to measure the decompressed fluid sample mid-infrared light absorbance and to generate a signal representing the carbon dioxide concentration.

* * * * *